United States Patent [19]

Rousseau

[11] Patent Number: 4,508,155

[45] Date of Patent: Apr. 2, 1985

[54] APPARATUS FOR AND METHOD OF OBTAINING IMPROVED DENTAL CASTINGS

[76] Inventor: Carl H. Rousseau, 2648 South Dr., Clearwater, Fla. 33519

[21] Appl. No.: 385,025

[22] Filed: Jun. 4, 1982

[51] Int. Cl.³ .................. B22C 7/02; B22C 9/04; B22C 21/00
[52] U.S. Cl. ..................... 164/35; 164/237; 164/244; 164/376; 164/377
[58] Field of Search ............ 164/237, 239, 244, 376, 164/377, DIG. 4, DIG. 15, 350, 35; 249/54, 110, 119, 173; 433/34

[56] References Cited

U.S. PATENT DOCUMENTS

| | | | |
|---|---|---|---|
| 539,209 | 5/1895 | Adams | 164/350 |
| 1,804,401 | 5/1931 | Davis | 164/237 |
| 1,970,261 | 8/1934 | Turner | 164/376 |
| 2,193,357 | 3/1940 | Greth | 164/376 |
| 2,195,960 | 4/1940 | Morris | 164/350 X |
| 2,267,329 | 12/1941 | Fowler et al. | 164/376 |
| 3,985,178 | 10/1976 | Cooper | 164/244 X |
| 4,081,019 | 3/1978 | Kulig | 164/244 X |
| 4,161,208 | 7/1979 | Cooper | 164/244 |

*Primary Examiner*—Nicholas P. Godici
*Assistant Examiner*—J. Reed Batten, Jr.
*Attorney, Agent, or Firm*—Frijouf, Rust & Pyle

[57] ABSTRACT

The apparatus comprises an expandable investment ring having a removable base. Formed on the top surface of the base, and within the void defined by the ring, is an indexed sprue former. A curved runner bar having an indexed coping is formed at one end thereof in mating relation to the sprue former. By virtue of this apparatus extremely accurate base metal castings may be obtained. The apparatus is also useful for preparing precious metal castings.

10 Claims, 9 Drawing Figures

APPARATUS FOR AND METHOD OF OBTAINING IMPROVED DENTAL CASTINGS

BACKGROUND OF THE INVENTION

1. Field of the Invention

The present invention relates to an apparatus and method useful for obtaining improved dental castings according to the lost wax method. The apparatus and method of this invention are particularly useful in that they permit dental castings of extreme accuracy to be prepared using base metal alloys rather than precious metals such as, for example, gold.

2. Description of the Prior Art

Various techniques and forms of apparatus are old and well known for preparing castings according to the lost wax method. Use of the lost wax method within the dental profession for the purpose of casting crowns and other such dental restorations is similarly well known. Of particular note with regard to dental castings is the fact that dental castings require extreme accuracy in the final product. Accordingly, metallurgical characteristics have virtually dictated that the castings be prepared from precious metals such as, for example, gold. Numerous attempts have been made at preparing dental castings from base metal alloys, but, again primarily due to metallurgical characteristics, base metal castings generally require excessive finish work so that the restoration will fit properly.

Yet another problem inherently present in all casting techniques utilizing the lost wax method is the fact that curing of the investment material is an exothermic reaction. That is to say, as the investment material hardens, heat is generated. This necessarily results in "swelling" of the investment material, and this usually results in at least some compression of the wax model within the investment. The compression against the wax model for a dental restoration will have an undesirable effect, for it will tend to distort the restoration pattern. Then, when the pattern is burned out and the molten metal is cast into the void formed within the hardened investment material, the casting thereby obtained will not correspond exactly to the original pattern. This results not only in discomfort to the patient for whom the restoration has been prepared, but unnecessary expenditure of time, energy and money for the patient, the dentist, and the dental technician.

Insofar as the problem of obtaining accurate castings utilizing base metal alloys is concerned, the only effective solution available today involves either detailed and expensive hand-finishing of the casting, the taking of new impressions and making new castings, or simply accepting a relatively inferior final product. Of course, another solution to this problem would be to prepare all castings from gold rather than a base metal alloy, but this obviously has an adverse economic impact on the patient.

Insofar as the expansion problems associated with the exothermic reaction whereby the investment material solidifies, prior patent literature does offer some suggestive solutions. U.S. Pat. No. 2,337,036 to Erdle discloses the use of a resilient mold for making porcelain dental restorations. While analogous to the field of preparing dental restorations, the resilient mold of this patent would not appear to be suitable for metal castings according to the lost wax process. Summy in U.S. Pat. No. 2,243,445 discloses an expansible absorbent receptacle for investments. U.S. Pat. No. 2,450,567 to Schwartz discloses a two-part flask for retaining investment material. Yet another casting ring constructed and arranged to prevent breakage of an investment made therein is disclosed in U.S. Pat. No. 1,976,655 to Carpenter. While no doubt useful for their stated purposes and in light of their various disclosures, none of these patents truly solve the problems associated with dental castings prepared utilizing the lost wax method and base metal alloys.

While the teachings of these patents do disclose apparatus including investment ring constructions whereby the investment material may expand, the structures disclosed are unnecessarily complicated. Furthermore, none of these prior art teachings make any attempt to solve the problem created by the fact that as the exothermic reaction takes place for solidifying the investment material, and as the wax pattern is subsequently burned out from within the investment material, different areas within the volume defined by the investment experience different temperatures. For the purpose of obtaining consistent, reproducible quality of final castings, it is desirable that the wax pattern, and the resulting casting mold, be formed at about the center of the investment material. While this is relatively easy to accomplish when, for example, a single crown is being cast, problems are encountered if one wishes to cast more than a single crown at a time, or if one is casting a larger restoration such as, for example, a bridge. This problem of variable temperature zones within the investment simply does not appear to have been dealt with in the prior art.

It is therefore apparent that there is a need in the prior art for improved means for preparing dental castings. The need is especially great with regard to the preparation of dental castings from base metal alloys, and is even greater when it is desired to cast more than a single restoration at a time. Of course, because utilization of the lost wax process invariably results in destruction of some casting material, it would be further desirable if at least some parts of the improved apparatus were reusable.

SUMMARY OF THE INVENTION

The present invention relates to apparatus for obtaining improved dental castings according to the lost wax method, and is especially suited for preparing castings from base metal alloys such as, for example, nickel-chromium-beryllium alloys. It is, however, to be understood that the apparatus of this invention is also suitable for use in preparing precious metal castings. By virtue of the apparatus construction set forth hereinafter, and utilizing standard lost wax procedures, a metal casting is repeatedly obtainable that will withstand examination under a 25 power stereoscopic microscope and demonstrate virtually absolute integrity of the marginal area. For example, base metal castings prepared utilizing the apparatus of this invention exhibit size variance of less than 10 microns, while the current state of the art in casting dental restorations accepts variance as great as 100 microns.

A first essential element of the apparatus of this invention is the investment ring defined by a substantially columnar tube open at each end thereof and including a fracture along its entire longitudinal dimension. As will be explained in greater detail below, the fracture is initially sealed with a wax prior to pouring the investment material, and then as the investment material hardens and releases heat, the entire ring may expand.

The apparatus further comprises base means defined by a substantially circular plate having a top and bottom surface. A lip is formed around the perimeter of the plate and extends upwardly from the plate's top surface. The inside diameter of the base means is greater than the outside diameter of the investment ring so that the ring may be placed therein prior to pouring the investment material. Just as the investment ring seam is sealed with wax prior to pouring, so is the entire perimeter seam between the investment ring and the base means. A sprue former is disposed on the top surface of the circular plate, and the sprue former includes an index tip formed thereon. As will also be explained in greater detail below, the purpose of the sprue former's index tip is to insure relative disposition of the wax pattern within the apparatus in a predetermined fashion so as to minimize the effect of any "hot" or "cold" spots during the course of conducting the lost wax casting technique.

The apparatus further comprises runner bar means attachable to the sprue former for holding the wax patterns within the poured investment material. In a basic embodiment the runner bar means comprises a curved proximal end including a coping integrally formed thereon, and an elongate bar extending away from the curved proximal end and terminating in a distal end. The coping includes an index receiver formed thereon whereby placement of the runner bar means onto the sprue former is predetermined, thereby resulting in predetermined orientation of the elongate bar and wax patterns attached thereto by sprue segments. Both the construction of the runner bar means and the relative position of attachment of sprue segments to the elongate bar thereof are quite important to the efficacy of this invention.

For the primary purpose of insuring a controlled, regulated flow of molten alloy into the investment, the curvature of the proximal end of the runner bar means defines an angle of about 55°-65° with respect to the elongate bar. Laboratory testing of the apparatus of this invention has confirmed that this construction serves to control and regulate the flow of molten alloy in a fashion such that damage to the prepared mold is virtually eliminated and extremely accurate castings are obtained. It should also be noted that the plane defined by the elongate bar is substantially parallel to the plane defined by the top of the coping. Furthermore, sprue segments utilized for attaching the wax patterns to the elongate bar are disposed so as to define an angle of about 50°-90° with respect to the elongate bar's distal end. Again, this relative attachment of the wax patterns to the elongate bar is primarily for the purpose of both directing and controlling the flow of molten alloy.

While this brief description has been given with regard to a single runner bar means and the casting of a single dental restoration, it is to be understood that, as will be explained in greater detail below, a relatively large variety of castings can be made utilizing alternative embodiments of this apparatus. For example, two or more crowns may be cast along a single elongate bar. In another embodiment, the runner bar means may comprise a corresponding pair of curved proximal ends, each being integrally attached to the same coping, and each further comprising a corresponding pair of elongate bars. In this embodiment at least as many as eight (8) dental restorations may be cast at a single time. It should be noed that when the runner bar means comprises such a corresponding pair of curved proximal ends and elongate bars, the angle defined by each of the proximal ends with respect to the plane defined by the top of the coping is about 60°. This construction is provided in order to maintain a condition of relative equilibrium within the investment, both in terms of internal temperature and contraction/expansion, during the casting technique. In yet another embodiment the runner bar means may comprise an elongate curved bar extending substantially from its mid point from the curved proximal end and terminating in a pair of oppositely disposed distal ends. This embodiment is particularly useful when casting a full arch.

The invention accordingly comprises the features of construction, combination of elements, and arrangements of parts which will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which.

Similar reference characters refer to similar parts throughout the several views of the drawings.

DETAILED DESCRIPTION

Figure 1:
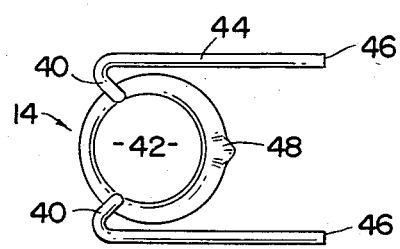
FIG. 1 is a top plan view of one embodiment of the runner bar means of this apparatus.
Figure 5:
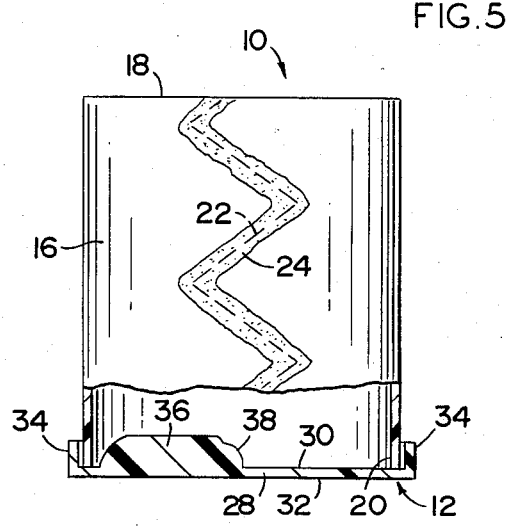
FIG. 5 is an elevational view, partially in section, illustrating the investment ring mounted on the base means.

As perhaps most clearly seen in the views of FIGS. 1 and 5, the apparatus for obtaining improved dental castings comprises an investment container or ring generally indicated as 10, base means generally indicated as 12, and runner bar means generally indicated as 14. Considering first the investment ring 10, and with regard to the views of FIGS. 5 and 6, it can be seen that ring 10 is defined by a substantially columnar tube 16 having a second open end 18 and a first open end 20 thereof. A fracture, or seam, 22 extends along the longitudinal dimension of tube 16 from open end 18 to open end 20. As seen in the view of FIG. 5, fracture 22 is preferably formed along a zig-zag path. Fracture 22 is shown in phantom in the view of FIG. 5 for the reason that this figure illustrates the application of heat sealing means shown as wax 24 over the outside of tube 16 along fracture 22 for sealing purposes prior to pouring the investment material (not shown in FIG. 5, but designated 26 in the view of FIG. 6).

Base means 12 comprises a substantially circular plate 28 having a top surface 30 and a bottom surface 32. A lip 34 is formed around the perimeter of plate 28 and extends upwardly from top surface 30 in substantially perpendicular relation thereto. As clearly seen in the view of FIG. 5, the inside diameter of base means 12 is greater than the outside diameter of tube 16 so that the investment ring 10 may be disposed within the base means 12.

Base means 12 further comprises a sprue former 36 integrally formed on top surface 30, and sprue former 36 includes an index tip 38 formed thereon. The function of sprue former 36 and index tip 38 will be described in greater detail hereinafter.

Figure 2:
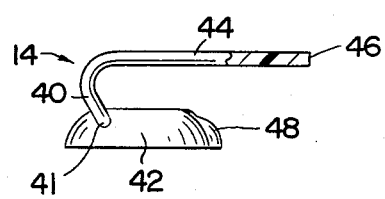
FIG. 2 is a side view of the runner bar means shown in the view of FIG. 1.

Finally, runner bar means 14 is most clearly illustrated in the views of FIGS. 1-4, inclusive. As best seen in the view of FIG. 2, runner bar means 14 comprises a curved proximal end portion 40 having a proximal end 41 connected to a coping 42, and distal end portion 44 extending from curved proximal end portion 40 and terminating in a distal end 46. Coping 42 further comprises an indexed receiver 48 formed thereon whereby the runner bar means 14 may be operatively disposed over sprue former 36 of base means 12 with the index receiver 48 in mating relation to index tip 38. Of course, as is clearly illustrated in the views of FIGS. 1 and 3, the runner bar means of this invention comprises a corresponding pair of curved proximal end portions 40, distal end portions 44, and distal ends 46. It is to be understood that there is no intention of limiting the scope of the present invention to such a paired construction. The runner bar means 14 may certainly comprise a single curved proximal end portion 40, distal end portion 44, and distal end 46. In such an embodiment it is contemplated that curved proximal end 40 would be connected to coping 42 such that distal end portion 44 would substantially bisect the top of the coping 42 when viewed in top plan similar to that of FIG. 1.

Figure 3:
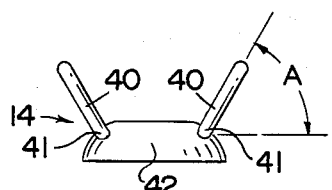
FIG. 3 is an end view of the runner bar means shown in the view of FIG. 1.

Inasmuch as this preferred embodiment does, however, comprise a paired construction, attention is invited to the view of FIG. 3 wherein the relative disposition of the two curved proximal end portions 40 with respect to the plane defined by the top of coping 42 may be seen. This angular relationship has been indicated by angle A and preferably is about 60°. By virtue of this construction, wax patterns 50, and the voids created thereby according to lost wax methods, are positioned within investment material 26 so as to minimize adverse effects of heating, cooling, compression, and expansion.

Figure 7:
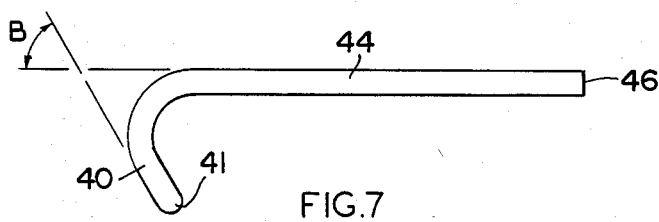
FIG. 7 is an enlarged, detailed view of the curved proximal end and elongate bar of the runner bar means for the purpose of illustrating the angular relationship therebetween.

Also of special note, and as best seen in the view of FIG. 7, the curvature of proximal end portion 40 defines an angle of about 55°-65° with respect to distal end portion 44. Angle B in the view of FIG. 7 identifies this angular relationship which is preferably about 57°. As already stated, above, this angular relationship between proximal end portion 40 and distal end portion 44 serves to control and regulate the flow of molten alloy into the mold cavity to insure base metal alloy castings of extremely high accuracy. Accordingly, this angular relationship B is present in all embodiments of the apparatus of this invention.

Figure 4:
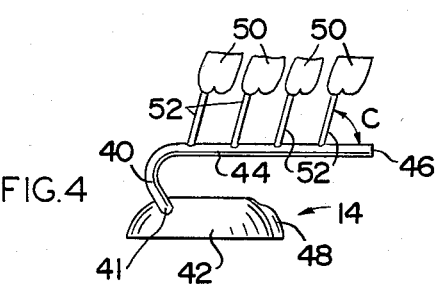
FIG. 4 is a side view similar to that of FIG. 2 illustrating the attachment of wax patterns by sprue segments to the runner bar means.

Attention is now invited to the view of FIG. 4 wherein the means for attaching wax patterns 50 to distal end portion 44 is illustrated. While the physical means for attachment is quite standard and comprises segments 52 of sprue wax, the relative position of segments 52 with respect to distal end 46 is quite important to the efficacy of this apparatus. The angular relationship between segments 52 and distal end 46 is designated by angle C in the view of FIG. 4 and falls within the range of about 50°-90°. Preferably, this angle is about 75°. Again, as previously stated, angular relationship C is important for the purpose of controlling and regulating the flow of molten alloy into the cavities formed upon burning out wax patterns 50.

Figure 6:
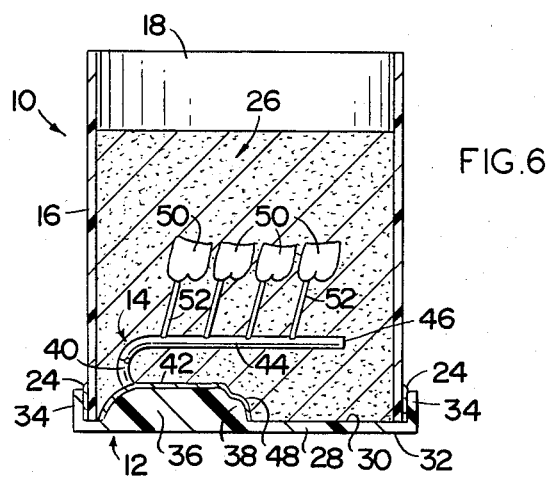
FIG. 6 is a sectional view of the apparatus after the investment material has been poured.

The sectional view of FIG. 6 illustrates the preferred embodiment of the apparatus of this invention in operative array. Once wax patterns 50 have been formed they are attached to the distal end portion 44 as previously described by sprue segments 52. The entire runner bar means 14 is then operatively disposed on sprue former 36 so that index receiver 48 and index tip 38 are in registry. Appropriate quantities of wax 24 may be utilized as the means for attaching coping 42 in position on sprue former 36. Next, investment ring 10 is mounted on base means 12, fracture 22 is closed by the application of wax 24, and tube 16 is sealed to lip 34 by additional quantities of wax 24. Next, previously prepared investment material is poured into the cavity defined by tube 16 and plate 28 to a depth of about 5 mm (one quarter inch) above wax patterns 50. Standard procedures are utilized during the addition of investment material 26 to insure complete filling of the cavity. After the filled apparatus has been allowed to set for about 1 hour, expansion of the investment ring along fracture 22 may be observed. Wax 24, both along fracture 22 and adjacent lip 34 will yield to permit such expansion, thereby virtually eliminating adverse compression forces on wax patterns 50. At this point investment ring 10 and base means 12 may be removed for final preparation of the casting mold according to standard lost wax techniques.

Figure 8:
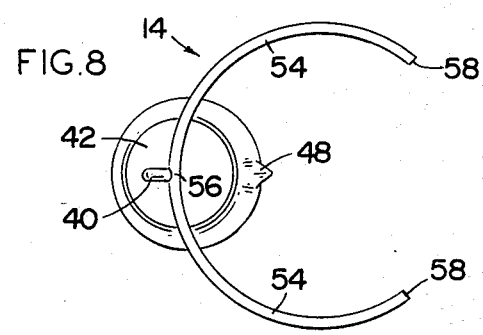
FIG. 8 is a top plan view, similar to that of FIG. 1, illustrating another embodiment for the runner bar means.
Figure 9:
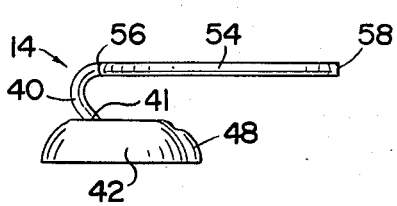
FIG. 9 is a side view of the runner bar means shown in FIG. 8.

The views of FIGS. 8 and 9 illustrate another embodiment for runner bar means 14. In this embodiment those elements corresponding to the embodiment of FIG. 1 which are identical thereto have been identified by corresponding reference numerals. The significant distinction between the embodiment of FIGS. 8 and 9 and that of FIG. 1 resides in the construction of the curved distal and portion 54. As clearly seen in the view of FIG. 8, curved distal end portion 54 is integrally formed on the proximal end 40 as at midpoint 56 and terminates in a pair of oppositely disposed distal ends 58. This embodiment for runner bar means 14 would be utilized in combination with investment ring 10 and base means 12 substantially as described above, and is particularly useful for casting a full arch.

It will thus be seen that the objects set forth above, among those made apparent from the preceding description, are efficiently attained and, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention, as a matter of language, might be said to fall therebetween.

Now that the invention has been described,

What is claimed is:

1. An apparatus for the preparation of a dental casting from a dental pattern utilizing a curable investment material which undergoes an exothermic reaction and expansion upon curing; comprising:
- a resilient expandable investment ring means being comprised of a substantially columnar tube which is open at both ends and having a fracture extending along the entire longitudinal dimension thereof;
- said resilient expandable investment ring means being biased by said resiliency thereof to substantially close said fracture;
- a base means defined by a plate having a top and a bottom surface with a substantially circular lip extending from said top surface;
- said circular lip having an inside diameter which is greater than the outside diameter of said investment ring means;
- a sprue former disposed on said base means;
- a runner bar means having a proximal end portion and a distal end portion with said proximal end portion forming an angle with respect to said distal end portion;
- said proximal end portion being operatively disposed on said sprue former and with said distal end portion receiving the dental pattern; and
- said investment ring means being disposed on said top surface of said base means and being disposed about said runner bar means by placing one of the open ends of said columnar tube on said top surface of said base means enabling said columnar tube to expand at said fracture against said bias of said investment ring means to open said fracture to accommodate for the expansion of the investment material upon the exothermic reaction of the investment material.

2. An apparatus as set forth in claim 1, wherein said fracture of said resilient expandable investment ring means is formed in a zig-zag path.

3. An apparatus as set forth in claim 1, including a smooth bend in said runner bar means for forming said angle between said distal end portion relative to said proximal end portion.

4. An apparatus as set forth in claim 1, wherein said distal end portion of said runner bar means is substantially parallel to said top surface of said base means.

5. An apparatus as set forth in claim 1 wherein said angle between said distal end portion relative to said proximal end portion is approximately sixty degrees.

6. An apparatus as set forth in claim 1 wherein said distal end portion comprises a curved bar extending from the mid point thereof from said proximal end portion and terminating in a pair of oppositely disposed distal end portions; and
- said distal end portions extending along the inner diameter of said resilient expandable investment ring mean.

7. An apparatus for the preparation of a dental casting from a dental pattern utilizing a curable investment material which undergoes an exothermic reaction and expansion upon curing; comprising:
- a resilient expandable investment ring means being comprised of a substantially columnar tube which is open at both ends and having a fracture extending along the entire longitudinal dimension thereof;
- said resilient expandable investment ring means being biased by said resiliency thereof to substantially close said fracture;
- heat sealing means for sealing said fracture of said resilient expandable investment ring means at ambient temperature and for enabling expansion of said resilient expandable investment ring means upon the production of heat by the exothermic reaction of the investment material;
- a base means defined by a plate having a top and a bottom surface with a substantially circular lip extending from said top surface;
- said circular lip having an inside diameter which is greater than the outside diameter of said investment ring means;
- a sprue former disposed on said base means;
- a runner bar means having a proximal end portion and a distal end portion with said proximal end portion forming an angle with respect to said distal end portion;
- said proximal end portion being operatively disposed on said sprue former and with said distal end portion receiving the dental pattern; and
- said investment ring means being disposed on said top surface of said base means and being disposed about said runner bar means by placing one of the open ends of said columnar tube on said top surface of said base means enabling said columnar tube to expand at said fracture against said bias of said investment ring means to open said fracture to accommodate for the expansion of the investment material upon the exothermic reaction of the investment material.

8. An apparatus for the preparation of a dental casting from a dental pattern utilizing investment material comprising:
- an investment ring means being comprised of a substantially columnar tube which is open at both ends;
- a base means defined by a plate having a top and a bottom surface with a substantially circular lip from said top surface;
- a sprue former disposed on said base means;
- a runner bar means having a proximal end portion and a distal end portion with said proximal end portion forming an angle in the form of a smooth bend with respect to said distal end portion;
- said angle between said distal end portion and said proximal end portion being approximately sixty degrees;
- said proximal end portion being operatively disposed on said sprue former and with said distal end portion receiving the dental pattern;
- said distal end portion of said runner bar means being substantially parallel to said top surface of said base means; and
- said investment ring means being receivable on said top surface of said base means and being disposed about said runner bar means by placing one of the open ends of said columnar tube on said top surface of said base means.

9. An apparatus as set forth in claim 8 wherein said distal end portion comprises a curved bar extending from the mid point thereof from said proximal end portion and terminating in a pair of oppositely disposed distal end portions; and
- said distal end portions extending along the inner diameter of said investment ring means.

10. The method of preparing a dental casting from a dental pattern utilizing a curable investment material which undergoes an exothermic reaction and expansion upon curing, comprising the steps of:

placing the dental pattern in an expandable investment ring having a fracture extending along the longitudinal length of the investment ring;

biasing the investment ring to substantially close the fracture;

enclosing the dental pattern with the investment material;

apply a heat sensitive sealer to the investment ring to seal the fracture at ambient temperature and for allowing expansion of the fracture due to heat generated by the exothermic reaction during the curing of the investment material;

allowing the investment ring to expand against the biasing of the investment ring to accommodate for the expansion of the investment material during the exothermic reaction of curing of the investment material; and heating the investment material to remove the dental pattern.

* * * * *